United States Patent [19]

Joines et al.

[11] 4,195,641
[45] Apr. 1, 1980

[54] SPECTROSCOPIC ANALYSIS OF CHEMICAL SUBSTANCES

[76] Inventors: William T. Joines, 4010 Deepwood Cir., Durham, N.C. 27707; Larry W. Burton, 5315 Fairoaks Rd., Durham, N.C. 27712; Marc D. Rafal, 626 Pamlico St., Durham, N.C. 27701; Alexander Spock, 515 Duluth St., Durham, N.C. 27705

[21] Appl. No.: 860,983

[22] Filed: Dec. 15, 1977

[51] Int. Cl.² .............................................. A61B 5/00
[52] U.S. Cl. ................................... 128/632; 356/311; 356/417
[58] Field of Search .................. 356/85, 86, 311, 313, 356/417; 128/2 A, 2 E, 2 W, 2.1 R, 2.1 E, 632

[56] References Cited

U.S. PATENT DOCUMENTS

| | | | |
|---|---|---|---|
| 4,037,962 | 7/1977 | Grisar et al. | 356/86 |
| 4,071,020 | 1/1978 | Pugliese | 356/85 |

Primary Examiner—F. L. Evans
Attorney, Agent, or Firm—B. B. Olive

[57] ABSTRACT

An intense electric field is employed as the external source of energy in carrying to a spectroscopic analysis of a chemical composition. The substance to be analyzed is placed between an insulated conductive electrode and a ground reference. A high voltage is then applied to the electrode to generate an electric field of a predetermined intensity within the test sample. As a result of the energy absorbed, the constituents of the sample are caused to release their characteristic spectral emissions. These emissions are optically filtered to isolate the wavelength of interest which is passed to a light detector and registered on a photon counting system. The procedure is especially and uniquely applicable for conducting an in situ chemical analysis of human sweat, thus offering a valuable aid in the diagnosis of various medical abnormalities.

11 Claims, 3 Drawing Figures

SPECTROSCOPIC ANALYSIS OF CHEMICAL SUBSTANCES

BACKGROUND OF THE INVENTION

1. Field of the Invention

The invention relates generally to the analysis of chemical substances and, more particularly, to a novel method and apparatus for carrying out a non-destructive, spectroscopic analysis.

2. Description of the Prior Art

It is well known that when energy in any form is absorbed by a substance, the atoms and molecules of that substance emit a portion of the absorbed energy at selective frequencies determined by the difference in allowed energy states within the substance. Since each element or combination of elements exhibits a characteristic emission spectrum, this phenomenon can and has been used to identify the components of a chemical composition and their concentration in the composition.

For example, it is commonly known that when a chemical sample containing sodium is placed in an open flame, an intense yellow light is emitted which is found to be a pair of closely-spaced spectral lines with wavelengths near 589 nanometers. This particular spectral emission identifies the presence of sodium, and its intensity is proportional to the quantity of sodium present in the sample.

Because a flame is used as the external source of energy, the aforementioned technique is generally referred to as flame spectroscopy.

Although microwaves and other forms of energy have been used in spectroscopic procedures, insofar as we are aware, the applicability of an intense electric field as the sole source of energy for inducing a chemical substance to emit its characteristic electromagnetic radiation has not been exploited heretofore.

The use of an intense electric field has been reported in connection with a non-analogous photographic technique known as Kirlian or corona discharge photography (see article by S. D. Kirlian, et al., "Photography By Means of High Frequency Currents", at page 19 of *Galaxies of Life*, published 1973 by Interface, New York, New York).

Kirlian photography is a process in which a photographic film is first placed near or in direct contact with an object. An electric field in the order of $10^6$ volts per meter is then generated about the object to stimulate light emissions from the surrounding air which exposes the film. If color film is used, the colors obtained appear to form an aura or corona around the object image, which may or may not be related to the actual emission spectra generated from the atmosphere surrounding the object.

The intent and purpose of Kirlian photography is to observe corona spectra from the air surrounding an object. No attempt is made to stimulate electromagnetic emissions from the object itself or to identify and quantify such emissions if generated by accident. In contrast, the basic objective of the present invention is to identify and quantify the elements of a chemical substance. This is accomplished by establishing an intense electric field on and within the substance which stimulates the elements present therein, as opposed to the surrounding atmosphere, to emit their characteristic electromagnetic spectra. Through an analysis of these spectral emissions, the identity and quantity of elements present in the chemical substance are determined.

SUMMARY OF THE INVENTION

According to the invention, a non-destructive, spectroscopic analysis of a chemical substance is carried out by first positioning a test sample of the substance between a ground reference and a conductive electrode. A high voltage is then applied to the conductive electrode to generate an electric field on and within the chemical sample of at least $10^6$ volts per meter. As a result of the energy absorbed from the electric field, the constituents of the chemical substance are caused to emit their characteristic spectra of electromagnetic energy. These spectral emissions are then optically filtered to isolate the wavelengths which identify the chemical elements of interest and the light energy passed by the filter is transmitted to conventional light detectors for detection and measurement of intensity. Since the intensity of the detected light is proportional to the quantity of the chemical element from which it was emitted, the amount of that element in the test sample is readily ascertained.

In one embodiment, the invention provides a unique capability for conducting an in situ chemical analysis of human sweat. This capability has substantial medical significance in that it greatly facilitates the early recognition and diagnosis of cystic fibrosis and other medical abnormalities.

DETAILED DESCRIPTION OF THE INVENTION

Figure 1:
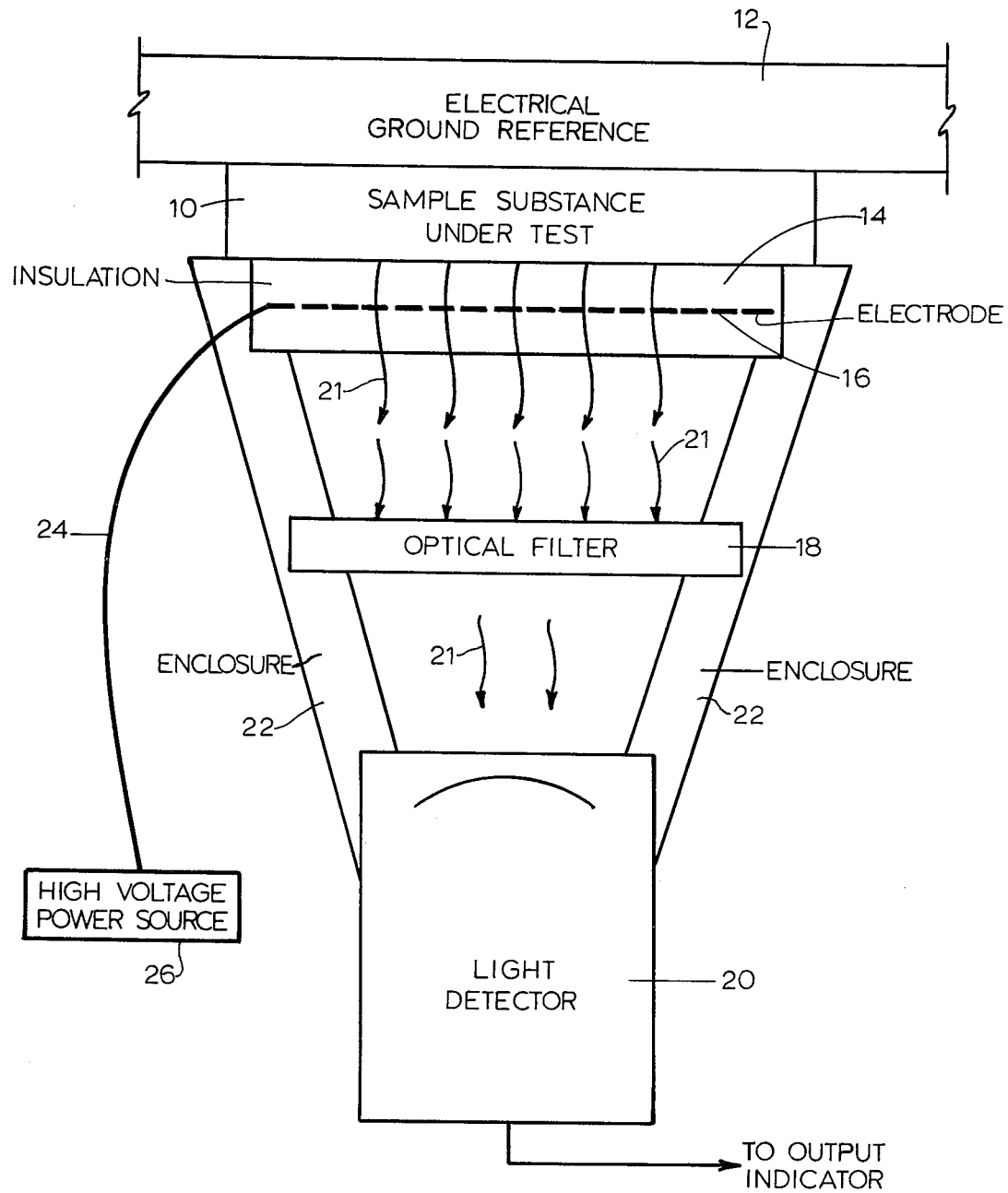
FIG. 1 is a schematic representation of an arrangement of the functional components of an apparatus suitable for carrying out the present invention.

The method of the invention and the manner and means by which it may be practiced will be best understood by reference to the accompanying drawings. Referring initially to FIG. 1, a test sample 10 is shown to be positioned between an electrical ground reference 12 and a transparent insulation material 14 which overlays semi-transparent, conductive electrode 16 which may, for example, be a glass encapsulated mesh electrode. Spaced below electrode 16 is an optical filter 18 which receives and filters a portion of the spectral emissions from the test sample and allows only the wavelengths of interest to pass to light detector 20 positioned beneath the filtering device 18. The flow path of the electromagnetic radiation emanating from test sample 10 is indicated in FIG. 1 by arrows 21. A light impervious enclosure 22 prevents any extraneous light from reaching the light detector 20.

In operating the system, a voltage appropriate for generating an electric field of at least $10^6$ volts per meter on the surface and within test sample 10 is applied to electrode 16. The voltage is supplied through electrical conduit 24 which connects electrode 16 with power source 26. Either an AC or DC voltage may be employed with AC being generally preferred. When employing an AC potential the frequency should be less than that at which electromagnetic resonance would be caused to occur in the chemical substance under test.

As a result of the energy absorbed from the applied electric field, the components of the chemical sample under test are stimulated to emit their characteristic optical spectra, a portion of which passes through electrode insulation 14 and the conductive electrode 16 to optical filter 18 which is designed to pass only the particular identifying wavelengths of interest to light detector 20. Since the output of the detector is proportional to the intensity of the radiation at the particular wavelength detected, it is, therefore, likewise proportional to the amount of the particular constituitive element of the chemical sample to which the detected radiation is attributable. Hence, within the range of resolution of the optical filter and the range of sensitivity of the light detector, the amount of any substance contributing to the chemical composition of the sample can be determined.

Figure 2:
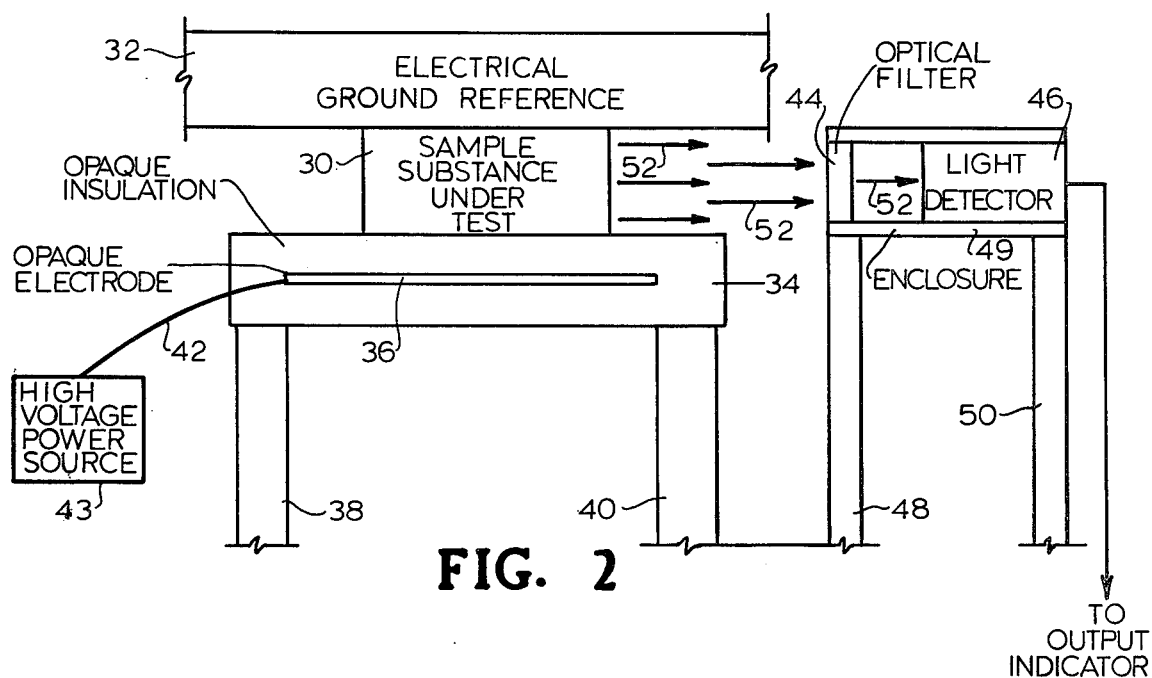
FIG. 2 is a schematic representation of an apparatus suitable for carrying out the invention in which an alternative arrangement of the functional components is shown.

In the alternative arrangement of the functional components such as illustrated in FIG. 2, the electrode and its insulation need not be transparent. As shown in FIG. 2, a test sample 30 is positioned between an electrical ground reference 32 and an opaque insulation material 34 encapsulating electrode 36, which is likewise opaque. An electrical conduit 42 connects electrode 36 with power source 43. Support for the assembly is provided by support members 38 and 40. An optical filter 44 and light detector 46 are positioned above electrode 36 and supported by support members 48 and 50 in a spaced horizontal alignment with test sample 30. Extraneous light is prevented from reaching the light detector by enclosure 49. In this arrangement the spectral emissions from the test sample do not flow downward but in the direction indicated by the arrows 52.

As previously noted, the invention herein described constitutes a valuable contribution to the field of clinical medicine in that it provides a capability for a rapid, simple and accurate analysis of human sweat in situ.

Sweat is a complex substance produced in the body by the eccrine glands which are present over most of the body surface and the apocrine glands which are found mainly in the axilla and perianal areas. The composition of sweat will vary, depending upon physiological and pathological conditions but urea, glucose, amino acids, sodium, potassium, chlorine, nitrogen, calcium, magnesium, phosphorous, iron, copper, manganese and certain other substances are generally present.

Since the sweat gland system is the predominant mechanism by which toxic metals are removed from the body, the existence of lead poisoning, for example, can be revealed by a chemical analysis of sweat excretions. In addition, abnormalities in sweat electrolytes are known to occur in adrenal cortical insufficiency, Wilson's disease, diabetes and especially in cystic fibrosis. In the case of cystic fibrosis, sweat analysis is the most reliable and primary technique of diagnosis.

Cystic fibrosis is a generalized disorder of the exocrine glands characterized by chronic pulmonary disease, pancreatic insufficiency and abnormally elevated sweat electrolytes. About one of two thousand children born in the United States are afflicted with the disease and as the basic defect remains unknown, there is no specific therapy. Nevertheless, increased knowledge of the disease has led to therapeutic measures which have extended and improved the life expectancy of the patient. Moreover, early detection of the problem in children has dramatically increased the average life expectancy so that fifty percent of those afflicted today can survive to the age of sixteen years with proper treatment.

As mentioned, a determination of the electrolyte levels in the sweat constitutes the single most reliable diagnostic test for the disease. Presently, these determinations are made by one of two basic techniques: directly by collecting and titrating a sample of sweat, or indirectly by conductivity measurements with ion selective electrodes.

The direct method requires that a sample of sweat be collected in a gauze patch, usually after the stimulation of sweating by iontophoresis of pilocarpine. The sample is then weighed, rinsed out of the gauze with a known volume of distilled water, and titrated to determine the concentration of either sodium or chloride. Because of the quantity of sample required, likelihood of error in weighing the sample and need to avoid contamination, the procedure requires a specially equipped laboratory with highly trained operators, and even then the results obtained are generally unreliable for children under seven months of age.

The alternative method involving conductivity measurements with ion selective electrodes offers the advantage of in situ analysis, but in general all methods using ion selective electrodes have proven to be unreliable with the unreliability usually being traceable to operator error. Thus, it can be concluded that presently available methods for analyzing the electrolyte content of eccrine sweat are subject to error as well as being time consuming and expensive. Moreover, they can not be applied to newborn infants.

According to the present invention, a method is provided for measuring the sodium concentration of human sweat in situ by a means which eliminates the deficiencies of the afore-described prior art procedures. Briefly, the method is practiced as follows: An appendage of the test subject, preferably the forearm, is first placed upon a glass-encapsulated mesh electrode. A high electrical potential is then applied to the electrode which stimulates the sodium present in the sweat to emit its characteristic atomic spectra. A portion of this radiation passes through the glass electrode to an optical filter where the radiation wavelength characteristic of sodium is separated from all other extraneous emissions. The sodium emission is then detected by a photomultiplier tube and registered on a photon counting system. Since the intensity of the sodium emission is directly related to the amount of sodium present, the concentration of this electrolyte in the sweat is accurately determined by simple calculation.

Because the procedure does not require the collection or handling of sweat samples, errors due to contamination are avoided. The analysis of the test results is objective and automated and therefore, the procedure is reliable even when carried out by unskilled operators. Moreover, the method is painless, can be conducted in less than five minutes, and is adaptable for the testing of newborn infants.

Figure 3:
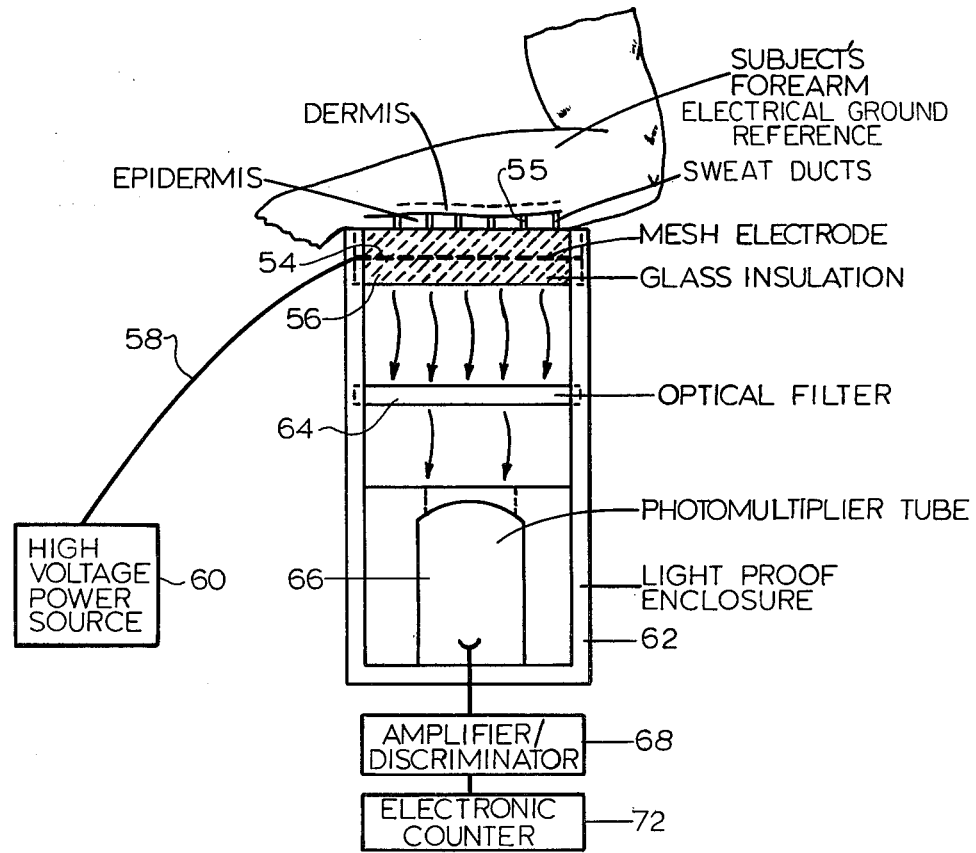
FIG. 3 illustrates schematically an arrangement of the component parts of an apparatus which is especially adapted for conducting an in situ chemical analysis of human sweat.

For a more detailed understanding of this particular embodiment of the invention reference is made to FIG. 3 of the drawings where a typical apparatus for conducting an in situ sweat analysis is shown in schematic representation. As seen, the components include a mesh electrode 54 encapsulated in a glass insulator 56 with electrical conduit 58 connecting the electrode with power source 60. Positioned beneath the glass encapsulated electrode 54 and within a light proof enclosure 62 are optical filter 64 and photomultiplier tube 66. Connected with and adapted to receive and process the electrical output from the photomultiplier tube 66 are a pulse amplifier/discriminator 68 and an electric counter 72. A computer (not shown) may be connected to electronic counter 72.

In carrying out an analysis to determine the sodium concentration in the sweat of a test subject, the subject's forearm is placed in contact with the glass insulation 56 which encapsulates the mesh electrode 54. The consistency, rate and amount of sweat from the forearm area makes this part of the body particularly desirable for testing. After the forearm is positioned, an electrical potential is then applied to the electrode appropriate for generating an electric field of at least $10^6$ volts per meter on the skin of the forearm. This intense electric field stimulates the sodium present in the sweat on the forearm to emit its characteristic spectra. A portion of this spectral emission passes through the glass-encapsulated electrode 54 to optical filter 64 which is adapted to restrict passage of all radiant energy except that at wavelengths approximately 589 nanometers, the emission characteristic of sodium. The sodium emission is then detected by photomultiplier tube 66 which transduces light energy into an electrical signal. The output signal from the photomultiplier tube is received by pulse amplifier/discriminator 68 and then passed to a photon counter 72 which can be connected to a computer (not shown). The computer readout may be recorded or displayed in any desired manner.

It has been found that the magnitude of electric field intensity on the surface of the sweat achieved for a given value of applied potential is strongly dependent upon the geometry of the intraepidermal sweat ducts (designated by the numeral 55 in FIG. 3) which are in contact with the glass insulation during the test operation. An intense electric field on the surface of the sweat in the duct is achieved by selecting a conductivity for the glass such that the individual sweat ducts behave as conducting posts in an essentially non-conducting media. Thus, even though the electric field is very intense on the surface of the sweat in the duct, the electric field in the internal portion of the duct is relatively small, thereby maintaining the conduction current density at a level below the threshold of pain or injury in the sensitive dermis area of the skin. As the subject begins to sweat profusely, the sweat pours out of the duct and commences to spread over the surface of the epidermis. The result of this is that the effective diameter of the conductive post begins to increase, thus lowering the magnitude of the electric field intensity on the surface of the sweat to a level below that normally corresponding to a given value of applied potential. Tolerance to these changes in the sweat duct geometry can be achieved by optimizing the conductivity of the glass insulation to maintain a maximum amount of potential gradient in the sweat duct consistent with the constraint that the duct must continue to appear as the conducting post. In general, if the conductivity of the glass insulation is greater than or equal to 0.001 times the conductivity of the skin, conduction current flow is adequately limited; and, if the conductivity of the glass is less than or equal to 0.1 times the conductivity of the skin, the intensity of the electric field on the skin is sufficient to stimulate optical emission from the sweat.

In practice, best results are achieved when the electric field is developed by applying an AC potential to the electrode whose frequency is less than that at which electromagnetic resonance would occur within the chemical constituents of the sweat composition being tested. The preference for an AC as opposed to a DC potential will be best understood from the following explanation of the mechanism by which sodium emissions are generated in this procedure.

Upon application of the external electric field, the sodium ions in the sweat are attracted to the cathode where they constitute an electrical conduction current by accepting an electron from the cathode. The now neutral sodium atoms remain in solution momentarily, then combine with hydroxyl ions to form sodium hydroxide. Within a hundreth second after the application of an external electric field, all sodium and other ions in the tonic sweat are depleted in this manner. Consequently, the only future source of sodium ions, and hence additional neutral sodium atoms, is from newly secreted sweat. Consider now what happens when an alternating electric field is applied. During the half cycle when the glass electrode represents the cathode, newly secreted sodium ions will be attracted to the surface of the intraepidermal ducts and neutralized as described above. Once transformed into neutral sodium atoms, the polarity of the electric field has little influence on the motion of the sodium. During the next half cycle, chlorine ions are attracted toward the glass electrode. Each chlorine ion is accelerated by virtue of the interaction of its charge with the externally applied electric field for some finite distance, whereupon it collides with another particle in the sweat. Upon collision, the kinetic energy of the chlorine ion will be imparted to the particle with which it collided. When such particle is a neutral sodium atom, this energy is radiated as a photon of light having a wavelength characteristic of the sodium from which it was emitted.

Since the mechanism by which the sodium spectrum is produced depends solely upon the sodium present in freshly secreted sweat, this greatly contributes to the accuracy of the test in that it eliminates error caused by foreign substances present on the body surface being tested or from accumulated body salt.

Given the broad instrumentation concepts as described and illustrated herein, those skilled in the art will recognize that all of the essential components are well known, standard items of commerce.

What is claimed is:

1. A method for carrying out a non-destructive, spectroscopic analysis of a chemical substance which comprises:
    (a) positioning a test sample of the chemical substance to be analyzed between an insulated conductive electrode and a ground reference;
    (b) stimulating the components of said chemical test sample to emit their characteristic optical spectra by establishing an electric field on and within said sample of at least $10^6$ volts per meter with said electric field being generated by the application of an appropriate potential to said insulated electrode;
    (c) filtering the optical spectra emitted from said test sample to segregate for further processing those spectral emissions having a selective wavelength which identifies the chemical element of interest;
    (d) detecting the emitted light energy at said selected wavelengths; and (e) determining the intensity of said detected light energy as a measure of the concentration of said chemical element in said chemical substance.

2. The method according to claim 1 wherein a DC potential is applied to said insulated electrode to generate said electric field.

3. The method according to claim 1 wherein an AC potential having a frequency less than that at which electromagnetic resonance would be caused to occur in said chemical test sample is applied to said insulated electrode to generate said electric field.

4. A method for carrying out a chemical analysis of human sweat in situ which comprises:
   (a) positioning an appendage of the human body such that a portion of the skin thereof is in contact with a glass-encapsulated, conductive electrode;
   (b) stimulating the chemical constituents present in the sweat secreted from the intraepidermal sweat ducts to emit their characteristic optical spectra by establishing an electric field of at least $10^6$ volts per meter on said portion of skin in contact with said glass-encapsulated electrode, and wherein said electric field is generated by applying an AC potential of appropriate magnitude to said electrode with the frequency of the applied potential being less than that at which electromagnetic resonance would be caused to occur within the sweat being tested;
   (c) filtering the optical spectra emitted from the sweat secreted from the intraepidermal ducts of the skin in contact with said glass-encapsulated electrode to isolate selective wavelengths which are identified with a particular chemical constitutent of interest in said sweat;
   (d) detecting the emitted light energy at said selective wavelengths; and
   (e) determining the intensity of said detected light energy as a measure of the concentration of said chemical constituent within said sweat.

5. The method according to claim 4 wherein a forearm of the human body is positioned such that a portion of the skin thereof is in contact with said glass-encapsulated electrode.

6. The method according to claim 4 wherein said selective wavelengths are those approximating 589 nanometers which is an emission characteristic of sodium.

7. An apparatus for conducting a non-destructive, spectroscopic analysis of a chemical substance which comprises:
   (a) an electrode encapsulated with an electrical insulator;
   (b) means for positioning a test sample between said insulated electrode and an electrical ground reference;
   (c) power means for supplying said electrode with a voltage appropriate for generating an electric field on and within said test sample of at least $10^6$ volts per meter wherein the chemical constituents of said test samples are inducted to emit their characteristic optical spectra;
   (d) an optical filter positioned proximate said electrode and disposed to receive the light emitted from said test sample;
   (e) light sensor means disposed to receive the light emissions which are allowed to pass through said optical filter; and
   (f) means connected to the output of said sensor means for registering a measurement of the intensity of the light emissions received by said sensor means.

8. The apparatus according to claim 7 wherein the electrode and its insulation are opaque and wherein said optical filter and light sensor means are disposed above said electrode in horizontal alignment with said test sample.

9. The apparatus according to claim 7 wherein said electrode is semi-transparent and said insulator is transparent and said filter is positioned to receive said light after it has passed through said electrode and the electrical insulation which envelops it.

10. An apparatus for performing a spectroscopic, chemical analysis of human sweat in situ which comprises:
   (a) a conductive wire mesh electrode encapsulated in an electrical insulator consisting of transparent glass and wherein said glass-encapsulated electrode is adapted to support an appendage of the human body placed in contact with said glass insulation for analyzing the sweat secreted from the intraepidermal sweat ducts within the skin of said appendage;
   (b) power means for supplying said electrode with an appropriate AC voltage for generating an electric field of at least $10^6$ volts per meter on the skin of said appendage in contact with the glass insulation of said electrode and wherein the frequency at which said voltage is applied is less than that at which electromagnetic resonance would be caused to occur within the sweat being tested, and wherein as a result of the absorption of energy from the electric field the chemical constituents of said sweat are induced to emit their characteristic spectra;
   (c) an optical filter positioned beneath said electrode and disposed to receive the light emitted from said sweat after said light has passed through said wire mesh electrode and the transparent glass insulation in which said electrode is encapsulated;
   (d) light sensor means disposed to receive the light emissions which are allowed to pass through said optical filter; and
   (e) means connected to the output of said sensor means for registering a measurement of the intensity of the light emissions received by said sensor means.

11. The apparatus according to claim 10 wherein said glass insulation has an electrical conductivity of between 0.1 and 0.001 times the conductivity of the skin in contact therewith.

* * * * *

UNITED STATES PATENT AND TRADEMARK OFFICE
CERTIFICATE OF CORRECTION

PATENT NO. : 4,195,641
DATED : April 1, 1980
INVENTOR(S) : William T. Joines, et al It is certified that error appears in the above—identified patent and that said Letters Patent is hereby corrected as shown below:

In second line of Abstract "to" should be --out--.

Col. 5, line 61, second occurrence of "the" should be --a--.

Col. 6, line 18, "tonic" should be --toxic--.

Col. 8, line 1, "inducted" should be --induced--.

Signed and Sealed this

Twenty-third Day of September 1980

[SEAL]

Attest:

SIDNEY A. DIAMOND

Attesting Officer

Commissioner of Patents and Trademarks